(12) United States Patent
Zucherman et al.

(10) Patent No.: US 7,803,190 B2
(45) Date of Patent: *Sep. 28, 2010

(54) INTERSPINOUS PROCESS APPARATUS AND METHOD WITH A SELECTABLY EXPANDABLE SPACER

(75) Inventors: James F. Zucherman, San Francisco, CA (US); Ken Y. Hsu, San Francisco, CA (US); Charles J. Winslow, Walnut Creek, CA (US)

(73) Assignee: Kyphon SÀRL, Neuchatel (CH)

( * ) Notice: Subject to any disclaimer, the term of this patent is extended or adjusted under 35 U.S.C. 154(b) by 149 days.

This patent is subject to a terminal disclaimer.

(21) Appl. No.: 11/558,352

(22) Filed: Nov. 9, 2006

(65) Prior Publication Data

US 2007/0093830 A1  Apr. 26, 2007

Related U.S. Application Data

(63) Continuation of application No. 10/684,847, filed on Oct. 14, 2003, now Pat. No. 7,306,628.

(60) Provisional application No. 60/421,921, filed on Oct. 29, 2002.

(51) Int. Cl.
*A61F 2/44* (2006.01)

(52) U.S. Cl. .................. 623/17.11; 623/17.16

(58) Field of Classification Search ... 623/17.11–17.16; 606/248, 249, 247, 90, 246
See application file for complete search history.

(56) References Cited

U.S. PATENT DOCUMENTS

| 2,077,804 | A | 4/1937 | Morrison | |
|---|---|---|---|---|
| 2,456,806 | A | 12/1948 | Wolffe | 33/174 |
| 2,677,369 | A | 5/1954 | Knowles | 128/92 |
| 3,426,364 | A | 2/1969 | Lumb | 3/1 |
| 3,643,658 | A | 2/1972 | Steinemenan | 128/920 |
| 3,648,691 | A | 3/1972 | Lumb | 128/920 |
| 3,765,296 | A | * 10/1973 | Fischer | 411/49 |
| 3,779,239 | A | 12/1973 | Fischer et al. | |
| 3,867,728 | A | 2/1975 | Stubstad | 3/1 |
| 3,875,595 | A | 4/1975 | Froning | 3/1 |
| 4,011,602 | A | 3/1977 | Rybicki et al. | |
| 4,034,418 | A | 7/1977 | Jackson | 3/1.911 |
| 4,219,015 | A | 8/1980 | Steinemenan | 128/92 D |
| 4,237,875 | A | 12/1980 | Termanini | |

(Continued)

FOREIGN PATENT DOCUMENTS

CA    2015507    1/1991

(Continued)

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.

(Continued)

*Primary Examiner*—Pedro Philogene
(74) *Attorney, Agent, or Firm*—Coats and Bennett P.L.L.C.

(57) ABSTRACT

The present invention is an interspinous process implant with a selectably expandable spacer that can be placed between adjacent spinous processes.

15 Claims, 10 Drawing Sheets

U.S. PATENT DOCUMENTS

| | | | |
|---|---|---|---|
| 4,257,409 A | 3/1981 | Bacal et al. | |
| 4,289,123 A | 9/1981 | Dunn | |
| 4,309,777 A | 1/1982 | Patil | 3/1.91 |
| 4,349,921 A | 9/1982 | Kuntz | 3/1 |
| 4,369,769 A | 1/1983 | Edwards | 128/69 |
| 4,401,112 A | 8/1983 | Rezaian | 128/92 B |
| 4,455,690 A | 6/1984 | Homsy | 3/1 |
| 4,479,491 A | 10/1984 | Martin | 128/92 B |
| 4,501,269 A | 2/1985 | Bagby | 128/96 G |
| 4,502,161 A | 3/1985 | Wall | 623/18 |
| 4,553,273 A | 11/1985 | Wu | 623/18 |
| 4,554,914 A | 11/1985 | Kapp | 128/92 C |
| 4,573,454 A | 3/1986 | Hoffman | |
| 4,599,084 A | 7/1986 | Nashef | 623/16 |
| 4,599,086 A | 7/1986 | Doty | 623/17 |
| 4,604,995 A | 8/1986 | Stephens | 128/69 |
| 4,611,582 A | 9/1986 | Duff | 128/69 |
| 4,632,101 A | 12/1986 | Freedland | |
| 4,636,217 A | 1/1987 | Ogilvie | 623/17 |
| 4,643,178 A | 2/1987 | Nastari | 128/92 |
| 4,657,550 A | 4/1987 | Daher | 623/17 |
| 4,685,447 A | 8/1987 | Iversen | 128/1 R |
| 4,686,970 A | 8/1987 | Dove et al. | |
| 4,696,290 A | 9/1987 | Steffee | 128/69 |
| 4,714,469 A | 12/1987 | Kenna | 623/17 |
| 4,743,256 A | 5/1988 | Brantigan | 623/17 |
| 4,759,769 A | 7/1988 | Hedman et al. | |
| 4,772,287 A | 9/1988 | Ray | 623/17 |
| 4,790,303 A | 12/1988 | Steffee | 128/924 M |
| 4,827,918 A | 5/1989 | Olerud | |
| 4,834,757 A | 5/1989 | Brantigan | 623/17 |
| 4,863,476 A | 9/1989 | Shepperd | |
| 4,878,915 A | 11/1989 | Brantigan | 623/17 |
| 4,886,405 A | 12/1989 | Blomberg | |
| 4,892,545 A | 1/1990 | Day et al. | |
| 4,904,260 A | 2/1990 | Ray | 623/17 |
| 4,904,261 A | 2/1990 | Dove | 623/17 |
| 4,913,134 A | 4/1990 | Luque | 128/69 |
| 4,913,144 A | 4/1990 | Del Medico | |
| 4,923,471 A | 5/1990 | Morgan | 623/16 |
| 4,931,055 A | 6/1990 | Bumpus et al. | |
| 4,932,975 A | 6/1990 | Main | 623/17 |
| 4,936,848 A | 6/1990 | Bagby | 623/17 |
| 4,946,378 A | 8/1990 | Hirayama | 623/17 |
| 4,961,740 A | 10/1990 | Ray | 606/61 |
| 4,969,887 A | 11/1990 | Sodhi | |
| 4,969,888 A | 11/1990 | Scholten | 606/94 |
| 5,011,484 A | 4/1991 | Breard | 606/61 |
| 5,015,247 A | 5/1991 | Michelson | 606/61 |
| 5,015,255 A | 5/1991 | Kuslich | 623/17 |
| 5,026,373 A | 6/1991 | Ray | 606/61 |
| 5,035,716 A | 7/1991 | Downey | 623/17 |
| 5,047,055 A | 9/1991 | Bao | 623/17 |
| 5,055,104 A | 10/1991 | Ray | 606/61 |
| 5,059,193 A | 10/1991 | Kuslich | 606/61 |
| 5,059,194 A | 10/1991 | Michelson | 606/61 |
| 5,062,845 A | 11/1991 | Kuslich | 606/80 |
| 5,062,850 A | 11/1991 | MacMillan | 623/17 |
| 5,074,864 A | 12/1991 | Cozad | 606/54 |
| 5,084,049 A | 1/1992 | Asher et al. | 606/61 |
| 5,088,869 A | 2/1992 | Greenslade | 411/386 |
| 5,092,866 A | 3/1992 | Breard | 606/61 |
| 5,098,433 A | 3/1992 | Freedland | |
| 5,105,255 A | 4/1992 | Shannon | 357/68 |
| 5,122,130 A | 6/1992 | Keller | 606/61 |
| 5,123,926 A | 6/1992 | Pisharodi | 623/17 |
| 5,127,912 A | 7/1992 | Ray | 606/61 |
| 5,147,404 A | 9/1992 | Downey | 623/17 |
| 5,167,662 A | 12/1992 | Hayes | 606/61 |
| 5,167,665 A | 12/1992 | McKinney | 606/75 |
| 5,171,278 A | 12/1992 | Pisharodi | |
| 5,180,381 A | 1/1993 | Aust | 606/61 |
| 5,192,327 A | 3/1993 | Brantigan | 623/17 |
| 5,201,734 A | 4/1993 | Cozad et al. | |
| 5,258,031 A | 11/1993 | Salib | 623/17 |
| 5,263,953 A | 11/1993 | Bagby | 606/61 |
| 5,275,601 A | 1/1994 | Gogolewski | 606/72 |
| 5,290,312 A | 3/1994 | Kojimoto | 623/17 |
| 5,300,073 A | 4/1994 | Ray | 606/61 |
| 5,304,178 A | 4/1994 | Stahurski | 606/61 |
| 5,306,275 A | 4/1994 | Bryan | 606/61 |
| 5,306,309 A | 4/1994 | Wagner | 623/17 |
| 5,306,310 A | 4/1994 | Siebels | |
| 5,312,405 A | 5/1994 | Korotko et al. | |
| 5,352,225 A | 10/1994 | Yuan | 606/61 |
| 5,360,430 A | 11/1994 | Lin | |
| 5,366,455 A | 11/1994 | Dove | 606/61 |
| 5,387,213 A | 2/1995 | Breard | 606/61 |
| 5,390,683 A | 2/1995 | Pisharodi | 128/898 |
| 5,391,168 A | 2/1995 | Sanders | 606/61 |
| 5,395,370 A | 3/1995 | Muller et al. | |
| 5,395,372 A | 3/1995 | Holt | 606/61 |
| 5,403,316 A | 4/1995 | Ashman | |
| 5,415,661 A | 5/1995 | Holmes | 606/69 |
| 5,437,672 A | 8/1995 | Alleyne | 606/61 |
| 5,437,674 A | 8/1995 | Worcel et al. | |
| 5,439,463 A | 8/1995 | Lin | |
| 5,443,514 A | 8/1995 | Steffee | 623/17 |
| 5,454,812 A | 10/1995 | Lin | 606/61 |
| 5,456,722 A | 10/1995 | McLeod | 623/13 |
| 5,458,638 A | 10/1995 | Kuslich | 623/17 |
| 5,458,641 A | 10/1995 | Ramirez Jimenez | 623/17 |
| 5,458,643 A | 10/1995 | Oka | 623/18 |
| 5,468,242 A | 11/1995 | Reisberg | 606/69 |
| 5,470,333 A | 11/1995 | Ray | 606/61 |
| 5,491,882 A | 2/1996 | Walston | 29/419.1 |
| 5,496,318 A | 3/1996 | Howland | 606/61 |
| 5,505,732 A | 4/1996 | Michelson | 606/61 |
| 5,507,745 A | 4/1996 | Logroscino | 606/61 |
| 5,507,823 A | 4/1996 | Walston | 623/21 |
| 5,514,180 A | 5/1996 | Heggeness | 623/17 |
| 5,518,498 A | 5/1996 | Lindenberg et al. | |
| 5,527,312 A | 6/1996 | Ray | 606/61 |
| 5,531,747 A | 7/1996 | Ray | 606/61 |
| 5,534,028 A | 7/1996 | Bao | 623/17 |
| 5,534,029 A | 7/1996 | Shima | 623/17 |
| 5,540,689 A | 7/1996 | Sanders | 606/61 |
| 5,549,679 A | 8/1996 | Kuslich | 623/17 |
| 5,554,191 A * | 9/1996 | Lahille et al. | 623/17.11 |
| 5,562,662 A | 10/1996 | Brumfield et al. | |
| 5,562,735 A | 10/1996 | Margulies | |
| 5,562,736 A | 10/1996 | Ray | 623/17 |
| 5,571,191 A | 11/1996 | Fitz | 623/17 |
| 5,571,192 A | 11/1996 | Schonhoffer | |
| 5,577,995 A | 11/1996 | Walker | 601/120 |
| 5,584,832 A | 12/1996 | Schlapfer | 606/61 |
| 5,593,409 A | 1/1997 | Michelson | 606/61 |
| 5,601,553 A | 2/1997 | Trebing | 606/61 |
| 5,603,713 A | 2/1997 | Aust | 606/61 |
| 5,609,634 A | 3/1997 | Voydeville | 623/17 |
| 5,609,635 A | 3/1997 | Michelson | |
| 5,616,142 A | 4/1997 | Yuan | 606/61 |
| 5,623,984 A | 4/1997 | Nozaki | 164/457 |
| 5,628,756 A | 5/1997 | Barker, Jr. | 606/139 |
| 5,630,816 A | 5/1997 | Kambin | |
| 5,645,597 A | 7/1997 | Krapiva | 623/17 |
| 5,645,599 A | 7/1997 | Samani | 623/17 |
| 5,653,761 A | 8/1997 | Pisharodi | 623/17 |
| 5,653,762 A | 8/1997 | Pisharodi | |
| 5,653,763 A | 8/1997 | Errico et al. | |
| 5,658,286 A | 8/1997 | Sava | 606/61 |
| 5,658,335 A | 8/1997 | Allen | |
| 5,665,122 A | 9/1997 | Kambin | |
| 5,672,177 A | 9/1997 | Seldin | 606/71 |

| Patent No. | Date | Name | Class |
|---|---|---|---|
| 5,674,295 A | 10/1997 | Ray | 623/17 |
| 5,674,296 A | 10/1997 | Bryan | 623/17 |
| 5,676,702 A | 10/1997 | Ratron | 623/17 |
| 5,690,649 A | 11/1997 | Li | |
| 5,693,100 A | 12/1997 | Pisharodi | |
| 5,702,395 A | 12/1997 | Hopf | |
| 5,702,452 A | 12/1997 | Argenson et al. | |
| 5,702,455 A | 12/1997 | Saggar | 623/17 |
| 5,707,390 A | 1/1998 | Bonutti | |
| 5,716,416 A | 2/1998 | Lin | |
| 5,723,012 A | 3/1998 | Jeanson et al. | |
| 5,725,582 A | 3/1998 | Bevan | 623/17 |
| 5,741,261 A | 4/1998 | Moskovitz | 606/79 |
| 5,746,762 A | 5/1998 | Bass | |
| 5,755,797 A | 5/1998 | Baumgartner | |
| 5,766,251 A | 6/1998 | Koshino | 623/16 |
| 5,766,252 A | 6/1998 | Henry | 623/17 |
| 5,800,438 A | 9/1998 | Tuke | 606/90 |
| 5,800,547 A | 9/1998 | Schafer et al. | |
| 5,810,815 A | 9/1998 | Morales | |
| 5,824,098 A | 10/1998 | Stein | 623/20 |
| 5,836,948 A | 11/1998 | Zucherman | 606/61 |
| 5,849,004 A | 12/1998 | Bramlet | |
| 5,860,977 A | 1/1999 | Zucherman | 606/61 |
| 5,865,846 A | 2/1999 | Bryan | 623/17 |
| 5,876,402 A | 3/1999 | Errico | 606/61 |
| 5,876,404 A | 3/1999 | Zucherman | 606/61 |
| 5,879,396 A | 3/1999 | Walston | 623/21 |
| 5,885,299 A | 3/1999 | Winslow | 606/99 |
| 5,888,196 A | 3/1999 | Bonutti | |
| 5,888,224 A | 3/1999 | Beckers | 627/17 |
| 5,888,226 A | 3/1999 | Rogozinski | 623/17 |
| 5,951,555 A | 9/1999 | Rehak | 606/61 |
| 5,976,186 A | 11/1999 | Bao | 623/17 |
| 5,980,523 A | 11/1999 | Jackson | |
| 6,001,130 A | 12/1999 | Bryan | 623/17 |
| 6,022,376 A | 2/2000 | Assell | 606/61 |
| 6,030,162 A | 2/2000 | Huebner | 411/413 |
| 6,045,552 A | 4/2000 | Zucherman | 606/61 |
| 6,045,554 A | 4/2000 | Grooms | 606/73 |
| 6,048,204 A | 4/2000 | Klardie | 433/174 |
| 6,048,342 A | 4/2000 | Zucherman | 606/61 |
| 6,048,344 A | 4/2000 | Schenk | 606/73 |
| 6,068,630 A | 5/2000 | Zucherman | 606/61 |
| RE36,758 E | 6/2000 | Fitz | 623/17 |
| 6,074,390 A | 6/2000 | Zucherman | 606/61 |
| 6,090,112 A | 7/2000 | Zucherman | 606/61 |
| 6,099,531 A | 8/2000 | Bonutti | 606/87 |
| 6,113,639 A | 9/2000 | Ray | 623/17.16 |
| 6,126,689 A | 10/2000 | Brett | |
| 6,126,691 A | 10/2000 | Kasra et al. | |
| 6,127,597 A | 10/2000 | Beyar et al. | |
| 6,129,730 A | 10/2000 | Bono | 606/73 |
| 6,132,464 A | 10/2000 | Martin | 623/17 |
| 6,139,550 A | 10/2000 | Michelson | 606/69 |
| 6,149,652 A | 11/2000 | Zucherman | 606/61 |
| 6,152,926 A | 11/2000 | Zucherman | 606/61 |
| 6,152,927 A | 11/2000 | Farris | 606/61 |
| 6,156,038 A | 12/2000 | Zucherman | 606/61 |
| 6,156,067 A | 12/2000 | Bryan | 623/17.15 |
| 6,183,471 B1 | 2/2001 | Zucherman | 606/61 |
| 6,190,387 B1 | 2/2001 | Zucherman | 606/61 |
| 6,190,413 B1 | 2/2001 | Sutcliffe | |
| 6,190,414 B1 * | 2/2001 | Young et al. | 623/17.15 |
| 6,193,721 B1 | 2/2001 | Michelson | 606/70 |
| 6,200,322 B1 | 3/2001 | Branch | 606/96 |
| 6,206,922 B1 | 3/2001 | Zdeblick | 623/17.11 |
| 6,214,050 B1 | 4/2001 | Huene | |
| 6,217,580 B1 | 4/2001 | Levin | 606/71 |
| 6,224,602 B1 | 5/2001 | Hayes | 606/69 |
| 6,224,607 B1 | 5/2001 | Michelson | 606/96 |
| 6,228,900 B1 | 5/2001 | Shen | 522/153 |
| 6,234,705 B1 | 5/2001 | Troxell | 403/237 |
| 6,235,030 B1 | 5/2001 | Zucherman | 606/61 |
| 6,238,397 B1 | 5/2001 | Zucherman | 606/61 |
| 6,261,296 B1 | 7/2001 | Aebi | 606/90 |
| 6,280,444 B1 | 8/2001 | Zucherman | 606/61 |
| 6,293,949 B1 | 9/2001 | Justis | 606/61 |
| 6,306,136 B1 | 10/2001 | Baccelli | 606/61 |
| 6,332,882 B1 | 12/2001 | Zucherman | 606/61 |
| 6,332,883 B1 | 12/2001 | Zucherman | 606/61 |
| 6,336,930 B1 | 1/2002 | Stalcup et al. | |
| 6,348,053 B1 | 2/2002 | Cachia | |
| 6,352,537 B1 | 3/2002 | Strnad | 606/61 |
| 6,364,883 B1 | 4/2002 | Santilli | |
| 6,368,351 B1 * | 4/2002 | Glenn et al. | 623/17.15 |
| 6,371,984 B1 | 4/2002 | Van Dyke | 623/11.11 |
| 6,371,987 B1 | 4/2002 | Weiland et al. | |
| 6,375,682 B1 | 4/2002 | Fleischmann et al. | |
| 6,379,355 B1 | 4/2002 | Zucherman | 606/61 |
| 6,383,186 B1 | 5/2002 | Michelson | 606/69 |
| 6,395,030 B1 | 5/2002 | Songer | 623/17.11 |
| 6,398,783 B1 | 6/2002 | Michelson | 606/70 |
| 6,402,750 B1 | 6/2002 | Atkinson et al. | |
| 6,402,751 B1 | 6/2002 | Hoeck et al. | |
| 6,402,756 B1 | 6/2002 | Ralph | 606/71 |
| 6,416,776 B1 | 7/2002 | Shamie | 424/423 |
| 6,419,676 B1 | 7/2002 | Zucherman | 606/61 |
| 6,419,677 B2 | 7/2002 | Zucherman | 606/61 |
| 6,419,703 B1 | 7/2002 | Fallin | 623/17.11 |
| 6,419,704 B1 | 7/2002 | Ferree | |
| 6,428,542 B1 | 8/2002 | Michelson | 606/70 |
| 6,436,145 B1 | 8/2002 | Miller | 623/20.34 |
| 6,440,169 B1 | 8/2002 | Elberg et al. | 623/17.16 |
| 6,447,513 B1 | 9/2002 | Griggs | |
| 6,451,019 B1 | 9/2002 | Zucherman | 606/61 |
| 6,451,020 B1 | 9/2002 | Zucherman | 606/61 |
| 6,454,771 B1 | 9/2002 | Michelson | 606/70 |
| 6,458,131 B1 | 10/2002 | Ray | 606/61 |
| 6,478,796 B2 | 11/2002 | Zucherman | 606/61 |
| 6,500,178 B2 | 12/2002 | Zucherman | 606/61 |
| 6,514,256 B2 | 2/2003 | Zucherman | 606/61 |
| 6,520,991 B2 | 2/2003 | Huene | |
| 6,527,776 B1 | 3/2003 | Michelson | 606/70 |
| 6,554,833 B2 | 4/2003 | Levy | |
| 6,558,423 B1 | 5/2003 | Michelson | 623/17.11 |
| 6,558,686 B1 | 5/2003 | Darouiche | 424/423 |
| 6,565,570 B2 | 5/2003 | Sterett | 606/69 |
| 6,565,605 B2 | 5/2003 | Goble | 623/17.11 |
| 6,579,318 B2 | 6/2003 | Varga | 623/17.11 |
| 6,579,319 B2 | 6/2003 | Goble | 623/17.11 |
| 6,582,433 B2 | 6/2003 | Yun | 606/61 |
| 6,582,467 B1 | 6/2003 | Teitelbaum et al. | |
| 6,592,585 B2 | 7/2003 | Lee et al. | |
| 6,592,586 B1 | 7/2003 | Michelson | 606/71 |
| 6,610,091 B1 | 8/2003 | Reiley | 623/17.11 |
| 6,620,163 B1 | 9/2003 | Michelson | 606/61 |
| 6,626,944 B1 | 9/2003 | Taylor | 623/17.16 |
| 6,641,585 B2 | 11/2003 | Sato et al. | 606/61 |
| 6,645,207 B2 | 11/2003 | Dixon et al. | |
| 6,652,527 B2 | 11/2003 | Zucherman | 606/61 |
| 6,652,534 B2 | 11/2003 | Zucherman | 606/102 |
| 6,669,729 B2 | 12/2003 | Chin | 623/17.11 |
| 6,685,742 B1 | 2/2004 | Jackson | |
| 6,695,842 B2 | 2/2004 | Zucherman | 606/61 |
| 6,699,246 B2 | 3/2004 | Zucherman | 606/61 |
| 6,699,247 B2 | 3/2004 | Zucherman | 606/61 |
| 6,709,435 B2 | 3/2004 | Lin | |
| 6,712,819 B2 | 3/2004 | Zucherman | 606/61 |
| 6,712,852 B1 | 3/2004 | Chung | 623/17.11 |
| 6,723,126 B1 | 4/2004 | Berry | |
| 6,730,126 B2 | 5/2004 | Boehm, Jr. et al. | |
| 6,730,127 B2 | 5/2004 | Michelson | 623/17.16 |
| 6,733,534 B2 * | 5/2004 | Sherman | 623/17.16 |
| 6,736,818 B2 | 5/2004 | Perren et al. | |
| 6,746,485 B1 | 6/2004 | Zucherman | 623/17.16 |

| | | | | | |
|---|---|---|---|---|---|
| 6,752,831 B2 | 6/2004 | Sybert .................. 623/13.17 | 2004/0049281 A1 | 3/2004 | Reiley |
| 6,758,863 B2 | 7/2004 | Estes et al. | 2004/0087948 A1 | 5/2004 | Suddaby |
| 6,761,720 B1 | 7/2004 | Senegas .................. 606/61 | 2004/0097931 A1 | 5/2004 | Mitchell |
| 6,764,491 B2 | 7/2004 | Frey et al. ................ 606/85 | 2004/0116927 A1 | 6/2004 | Graf |
| 6,770,096 B2 | 8/2004 | Bolger et al. | 2004/0122427 A1 | 6/2004 | Holmes |
| 6,773,460 B2 * | 8/2004 | Jackson ................ 623/17.15 | 2004/0133204 A1 | 7/2004 | Davies |
| 6,783,527 B2 | 8/2004 | Drewry .................. 606/61 | 2004/0143268 A1 | 7/2004 | Falahee |
| 6,783,530 B1 | 8/2004 | Levy | 2004/0167625 A1 | 8/2004 | Beyar et al. |
| 6,796,983 B1 | 9/2004 | Zucherman .............. 606/61 | 2004/0181229 A1 | 9/2004 | Michelson |
| 6,800,670 B2 | 10/2004 | Shen ...................... 522/153 | 2004/0186475 A1 | 9/2004 | Falahee |
| 6,811,567 B2 | 11/2004 | Reiley ................. 623/17.11 | 2004/0210313 A1 | 10/2004 | Michelson |
| 6,835,205 B2 | 12/2004 | Atkinson et al. | 2004/0230201 A1 | 11/2004 | Yuan |
| 6,902,566 B2 | 6/2005 | Zucherman .............. 606/61 | 2004/0230304 A1 | 11/2004 | Yuan |
| 6,905,512 B2 | 6/2005 | Paes et al. | 2004/0236334 A1 | 11/2004 | Michelson |
| 6,926,728 B2 | 8/2005 | Zucherman et al. ........ 606/190 | 2004/0236335 A1 | 11/2004 | Michelson |
| 6,936,050 B2 | 8/2005 | Michelson ................ 606/61 | 2004/0260397 A1 | 12/2004 | Lambrecht et al. |
| 6,936,051 B2 | 8/2005 | Michelson ................ 606/61 | 2005/0010293 A1 | 1/2005 | Zucherman et al. |
| 6,946,000 B2 | 9/2005 | Senegas et al. | 2005/0027297 A1 | 2/2005 | Michelson |
| 6,949,123 B2 | 9/2005 | Reiley ................. 623/17.11 | 2005/0027298 A1 | 2/2005 | Michelson |
| 6,969,390 B2 | 11/2005 | Michelson ................ 606/61 | 2005/0049708 A1 | 3/2005 | Atkinson et al. |
| 6,972,019 B2 | 12/2005 | Michelson ................ 606/61 | 2005/0165398 A1 | 7/2005 | Reiley |
| 6,974,478 B2 | 12/2005 | Reiley et al. ........... 623/17.11 | 2005/0203512 A1 | 9/2005 | Hawkins et al. |
| 6,981,975 B2 | 1/2006 | Michelson | 2005/0203624 A1 | 9/2005 | Serhan et al. |
| 7,011,685 B2 | 3/2006 | Arnin et al. | 2005/0228391 A1 | 10/2005 | Levy et al. |
| 7,025,789 B2 | 4/2006 | Chow et al. ............ 623/21.11 | 2005/0245937 A1 | 11/2005 | Winslow |
| 7,041,105 B2 | 5/2006 | Michelson ................ 606/71 | 2005/0261768 A1 | 11/2005 | Trieu |
| 7,041,135 B2 | 5/2006 | Michelson ............. 623/17.11 | 2005/0288672 A1 | 12/2005 | Feree |
| 7,041,136 B2 | 5/2006 | Goble et al. ........... 623/17.11 | 2006/0004447 A1 | 1/2006 | Mastrorio et al. |
| 7,044,952 B2 | 5/2006 | Michelson ................ 606/71 | 2006/0004455 A1 | 1/2006 | Leonard et al. |
| 7,048,736 B2 | 5/2006 | Robinson et al. ........... 606/61 | 2006/0015181 A1 | 1/2006 | Elberg |
| 7,063,701 B2 | 6/2006 | Michelson ................ 606/73 | 2006/0064165 A1 | 3/2006 | Zucherman et al. |
| 7,063,702 B2 | 6/2006 | Michelson ................ 606/73 | 2006/0084983 A1 | 4/2006 | Kim |
| 7,074,237 B2 | 7/2006 | Goble et al. ........... 623/17.11 | 2006/0084985 A1 | 4/2006 | Kim |
| 7,077,844 B2 | 7/2006 | Michelson ................ 606/71 | 2006/0084987 A1 | 4/2006 | Kim |
| 7,081,120 B2 | 7/2006 | Li et al. | 2006/0084988 A1 | 4/2006 | Kim |
| 7,087,055 B2 * | 8/2006 | Lim et al. ................ 606/99 | 2006/0085069 A1 | 4/2006 | Kim |
| 7,087,083 B2 | 8/2006 | Pasquet et al. | 2006/0085070 A1 | 4/2006 | Kim |
| 7,087,084 B2 | 8/2006 | Reiley ................. 623/17.11 | 2006/0085074 A1 | 4/2006 | Raiszadeh |
| 7,090,698 B2 | 8/2006 | Goble et al. ........... 623/17.11 | 2006/0089654 A1 | 4/2006 | Lins et al. |
| 7,097,645 B2 | 8/2006 | Michelson ................ 606/71 | 2006/0089719 A1 | 4/2006 | Trieu |
| 7,097,648 B1 | 8/2006 | Globerman et al. | 2006/0095136 A1 | 5/2006 | McLuen |
| 7,101,375 B2 | 9/2006 | Zucherman et al. ........... 606/61 | 2006/0106381 A1 | 5/2006 | Ferree et al. |
| 7,101,398 B2 | 9/2006 | Dooris et al. ............ 623/13.11 | 2006/0106397 A1 | 5/2006 | Lins |
| 7,112,202 B2 | 9/2006 | Michelson ................ 606/71 | 2006/0111728 A1 | 5/2006 | Abdou |
| 7,115,130 B2 | 10/2006 | Michelson ................ 606/71 | 2006/0116690 A1 | 6/2006 | Pagano |
| 7,163,558 B2 | 1/2007 | Senegas et al. | 2006/0122620 A1 | 6/2006 | Kim |
| 7,163,561 B2 | 1/2007 | Michelson ............. 623/17.16 | 2006/0136060 A1 | 6/2006 | Taylor |
| 7,201,751 B2 | 4/2007 | Zucherman et al. | 2006/0184247 A1 | 8/2006 | Edidin et al. |
| 7,217,293 B2 | 5/2007 | Branch, Jr. | 2006/0184248 A1 | 8/2006 | Edidin et al. |
| 7,238,204 B2 | 7/2007 | Le Couedic et al. | 2006/0195102 A1 | 8/2006 | Malandain |
| 7,306,628 B2 * | 12/2007 | Zucherman et al. ....... 623/17.11 | 2006/0217726 A1 | 9/2006 | Maxy et al. |
| 7,335,203 B2 | 2/2008 | Winslow et al. | 2006/0235387 A1 | 10/2006 | Peterman |
| 7,377,942 B2 | 5/2008 | Berry | 2006/0235532 A1 | 10/2006 | Meunier et al. |
| 7,442,208 B2 | 10/2008 | Mathieu et al. | 2006/0241601 A1 | 10/2006 | Trautwein et al. |
| 7,445,637 B2 | 11/2008 | Taylor | 2006/0241613 A1 | 10/2006 | Brueneau et al. |
| 7,458,981 B2 | 12/2008 | Fielding et al. | 2006/0247623 A1 | 11/2006 | Anderson et al. |
| 7,582,106 B2 | 9/2009 | Teitelbaum et al. | 2006/0247640 A1 | 11/2006 | Blackwell et al. |
| 7,611,316 B2 | 11/2009 | Panasik et al. | 2006/0264938 A1 | 11/2006 | Zucherman et al. |
| 2001/0018614 A1 | 8/2001 | Bianchi | 2006/0271044 A1 | 11/2006 | Petrini et al. |
| 2002/0133155 A1 | 9/2002 | Ferree | 2006/0271049 A1 | 11/2006 | Zucherman et al. |
| 2002/0143331 A1 | 10/2002 | Zucherman et al. | 2006/0293662 A1 | 12/2006 | Boyer, II et al. |
| 2002/0151895 A1 | 10/2002 | Soboleski | 2006/0293663 A1 | 12/2006 | Walkenhorst et al. |
| 2002/0183756 A1 | 12/2002 | Michelson | 2007/0043362 A1 | 2/2007 | Malandain et al. |
| 2003/0040746 A1 | 2/2003 | Mitchell | 2007/0142915 A1 | 7/2007 | Altarac et al. |
| 2003/0065330 A1 | 4/2003 | Zucherman et al. | 2007/0151116 A1 | 7/2007 | Malandain |
| 2003/0153915 A1 | 8/2003 | Nekozuka et al. | 2007/0162000 A1 | 7/2007 | Perkins |
| 2004/0006391 A1 | 1/2004 | Reiley | 2007/0191838 A1 | 8/2007 | Bruneau et al. |
| 2004/0049273 A1 | 3/2004 | Reiley | 2007/0198091 A1 | 8/2007 | Boyer et al. |
| 2004/0049274 A1 | 3/2004 | Reiley | 2007/0225807 A1 | 9/2007 | Phan et al. |
| 2004/0049275 A1 | 3/2004 | Reiley | 2007/0233068 A1 | 10/2007 | Bruneau et al. |
| 2004/0049276 A1 | 3/2004 | Reiley | 2007/0233081 A1 | 10/2007 | Pasquet et al. |
| 2004/0049277 A1 | 3/2004 | Reiley | 2007/0233089 A1 | 10/2007 | DiPoto et al. |
| 2004/0049278 A1 | 3/2004 | Reiley | 2007/0270834 A1 | 11/2007 | Bruneau et al. |

| | | |
|---|---|---|
| 2007/0276369 A1 | 11/2007 | Allard et al. |
| 2007/0276493 A1 | 11/2007 | Malandain et al. |
| 2007/0282443 A1 | 12/2007 | Globerman et al. |
| 2008/0021457 A1 | 1/2008 | Anderson et al. |
| 2008/0058934 A1 | 3/2008 | Malandain et al. |
| 2008/0161818 A1 | 7/2008 | Kloss et al. |
| 2008/0183211 A1 | 7/2008 | Lamborne et al. |
| 2008/0183218 A1 | 7/2008 | Mueller et al. |
| 2008/0221685 A9 | 9/2008 | Altarac et al. |
| 2008/0262617 A1 | 10/2008 | Froehlich et al. |
| 2009/0234389 A1 | 9/2009 | Chuang et al. |
| 2009/0270918 A1 | 10/2009 | Attia et al. |

FOREIGN PATENT DOCUMENTS

| | | |
|---|---|---|
| DE | 2821678 A1 | 4/1980 |
| DE | 3113142 A1 | 1/1982 |
| DE | 3922044 A1 | 2/1991 |
| DE | 4012622 C1 | 7/1991 |
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |
| EP | 0307241 B1 | 12/1992 |
| EP | 0677277 A2 | 10/1995 |
| EP | 0767636 B1 | 4/1997 |
| EP | 1004276 A1 | 5/2000 |
| EP | 1138268 A1 | 10/2001 |
| EP | 1302169 A1 | 4/2003 |
| EP | 1330987 A1 | 7/2003 |
| EP | 1982664 A1 | 10/2008 |
| FR | 2623085 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2722087 A1 | 1/1996 |
| FR | 2722088 | 1/1996 |
| FR | 2722980 A1 | 2/1996 |
| FR | 2724554 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2780269 A1 | 12/1999 |
| FR | 2782911 A1 | 3/2000 |
| FR | 2799948 A1 | 4/2001 |
| FR | 2806614 A1 | 9/2001 |
| FR | 2806616 A1 | 9/2001 |
| FR | 2816197 A1 | 5/2002 |
| GB | 780652 | 8/1957 |
| JP | 02-224660 | 9/1990 |
| JP | 09-075381 | 3/1997 |
| JP | 10-179622 | 7/1998 |
| SU | 988281 | 1/1983 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 94/26193 | 11/1994 |
| WO | WO 94/26195 | 11/1994 |
| WO | WO 95/35067 | 12/1995 |
| WO | WO 96/08206 A1 | 3/1996 |
| WO | WO 96/39975 | 12/1996 |
| WO | 97/18769 | 5/1997 |
| WO | WO 98/20939 | 5/1998 |
| WO | WO 98/48717 | 11/1998 |
| WO | WO 98/55038 | 12/1998 |
| WO | WO 99/26562 | 6/1999 |
| WO | WO 99/40866 | 8/1999 |
| WO | WO 99/42051 | 8/1999 |
| WO | WO 99/56653 | 11/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/38582 | 7/2000 |
| WO | WO 00/44319 | 8/2000 |
| WO | WO 00/53126 | 9/2000 |
| WO | WO 01/26566 A1 | 4/2001 |
| WO | WO 01/28442 A1 | 4/2001 |
| WO | WO 01/54598 A1 | 8/2001 |
| WO | WO 02/34120 A2 | 5/2002 |
| WO | WO 02/051326 | 7/2002 |
| WO | WO 02/085226 A1 | 10/2002 |
| WO | WO 03/057055 A1 | 7/2003 |
| WO | WO 03/101350 A1 | 12/2003 |
| WO | WO 2004/047689 A1 | 6/2004 |
| WO | WO 2004/047691 A1 | 6/2004 |
| WO | WO 2004/071358 A1 | 8/2004 |
| WO | WO 2004/084768 A2 | 10/2004 |
| WO | WO 2004/098465 A1 | 11/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | 2009/083276 A1 | 7/2009 |
| WO | 2009/083583 A1 | 7/2009 |
| WO | 2009/098536 A1 | 8/2009 |

OTHER PUBLICATIONS

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Congress of Neurosurgery (EANS), Sep. 7-12, 2003, pp. 835-839, Lisbon, Portugal.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochirurgia, Advanced Peripheral Nerve Surgery and Minimal Invasive Spinal Surgery, Alexandre et al., eds., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Minns, R.J., et al., *Preliminary Design and Experimental Studies of a Novel Soft Implant for Correcting Sagittal Plane Instability in the Lumbar Spine*, SPINE vol. 22, No. 16, pp. 1819-1825, (c) 1997, Lippincott-Raven Publishers.

Haruo Tsuji, et al., *Ceramic Interspinous Block (CISB) Assisted Anterior Interbody Fusion*, Journal of Spinal Disorders, vol. 3, No. 1, pp. 77-86, (c)1990 Raven Press, Ltd., New York.

Richard W. Porter, MD, FRCS, FRCSE, *Spinal Stenosis and Neurogenic Claudication*, SPINE vol. 21, No. 17, pp. 2046-2052, (c)1996, Lippincott-Raven Publishers.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

INTERSPINOUS PROCESS APPARATUS AND METHOD WITH A SELECTABLY EXPANDABLE SPACER

CLAIM OF PRIORITY

This application is a continuation of U.S. patent application Ser. No. 10/684,847, entitled "Interspinous Process Apparatus and Method with Selectably Expandable Spacer," by Zucherman et al., filed Oct. 14, 2003, which claims benefit to U.S. Provisional Application No. 60/421,921, entitled "Interspinous Process Apparatus and Method with Selectably Expandable Spacer," by Zucherman et al., filed Oct. 29, 2002, both of which are incorporated herein by reference in their entireties.

CROSS REFERENCES TO RELATED APPLICATION

This application is related to U.S. patent application Ser. No. 10/037,236, filed Nov. 9, 2001, which is related to U.S. patent application Ser. No. 09/799,215, filed Mar. 5, 2001, now U.S. Pat. No. 7,101,375, issued Sep. 5, 2006, which is a related to U.S. patent application Ser. No. 09/179,570, filed Oct. 27, 1998, now U.S. Pat. No. 6,048,342, issued Apr. 11, 2000, which is related to U.S. patent application Ser. No. 09/175,645, filed Oct. 20, 1998, now U.S. Pat. No. 6,068,630, issued May 30, 2000. This application is also related to U.S. Pat. No. 5,836,948, issued Nov. 17, 1998 and U.S. Pat. No. 5,860,977, issued Jan. 19, 1999. All of the above are incorporated herein by reference.

FIELD OF THE INVENTION

This invention relates to an apparatus and method for adjustably distracting the spinous process of adjacent vertebrae.

BACKGROUND OF INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk, and arms to the pelvis and legs, (2) complex physiological motion between these parts, and (3) protection of the spinal cord and the nerve roots.

As the population ages, it is anticipated that there will be an increase in adverse spinal conditions characteristic in older persons. For example, with aging comes an increase in spinal stenosis (including, but not limited to, central canal and lateral stenosis), the thickening of the bones that make up the spinal column, and facet antropathy. Spinal stenosis is characterized by a reduction in the available space for the passage of blood vessels and nerves. Pain associated with such stenosis can be relieved by medication and/or surgery. Of course, it is desirable to eliminate the need for major surgery for all individuals, and, in particular, for the elderly.

In addition, there are a variety of other ailments that can cause back pain in patients of all ages. For these ailments it is also desirable to eliminate such pain without major surgery.

Accordingly, there is a need for a method for alleviating such conditions that is minimally invasive, can be tolerated by patients of all ages (in particular, the elderly), can be performed on an out-patient basis, and allows adjustments both during and after surgery to minimize patient discomfort. There is a further need for an apparatus with which to apply the method.

BRIEF DESCRIPTION OF THE DRAWINGS

FIG. 1A is a front plan view of one embodiment of an apparatus with a selectably expandable spacer; FIG. 1B is a left side view of the apparatus of FIG. 1A; FIG. 1C is a front plan view of the apparatus of FIG. 1A including a selectably expandable spacer, a main body and a first wing; FIG. 1D is a left side view of the second wing of the apparatus of FIG. 1A; FIG. 1E is a front plan view of the second wing of the apparatus of FIG. 1A; FIG. 1F is an end view of the selectably expandable spacer of the apparatus of FIG. 1A.

FIG. 2A is a right side view of an embodiment of the selectably adjustable spacer in an unexpanded position. FIG. 2B is a right side view of an embodiment of the selectably adjustable spacer in a fully expanded position.

FIG. 3A is a right side cross-sectional view of an embodiment of the selectably adjustable spacer in an unexpanded position. FIG. 3B is a left side cross-sectional view of an embodiment of the selectably adjustable spacer in a fully expanded position.

FIG. 6A is a right side view of an alternative embodiment of the selectably expandable spacer with a jack expansion mechanism in an unexpanded position. FIG. 6B is a right side view of an alternative embodiment of the selectably expandable spacer with a jack expansion mechanism in a fully expanded position.

FIG. 7 is a block diagram demonstrating the steps for performing the method, while

DETAILED DESCRIPTION OF THE PREFERRED EMBODIMENT

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents and patent applications cited in this application are incorporated herein by reference.

Figure 1A:
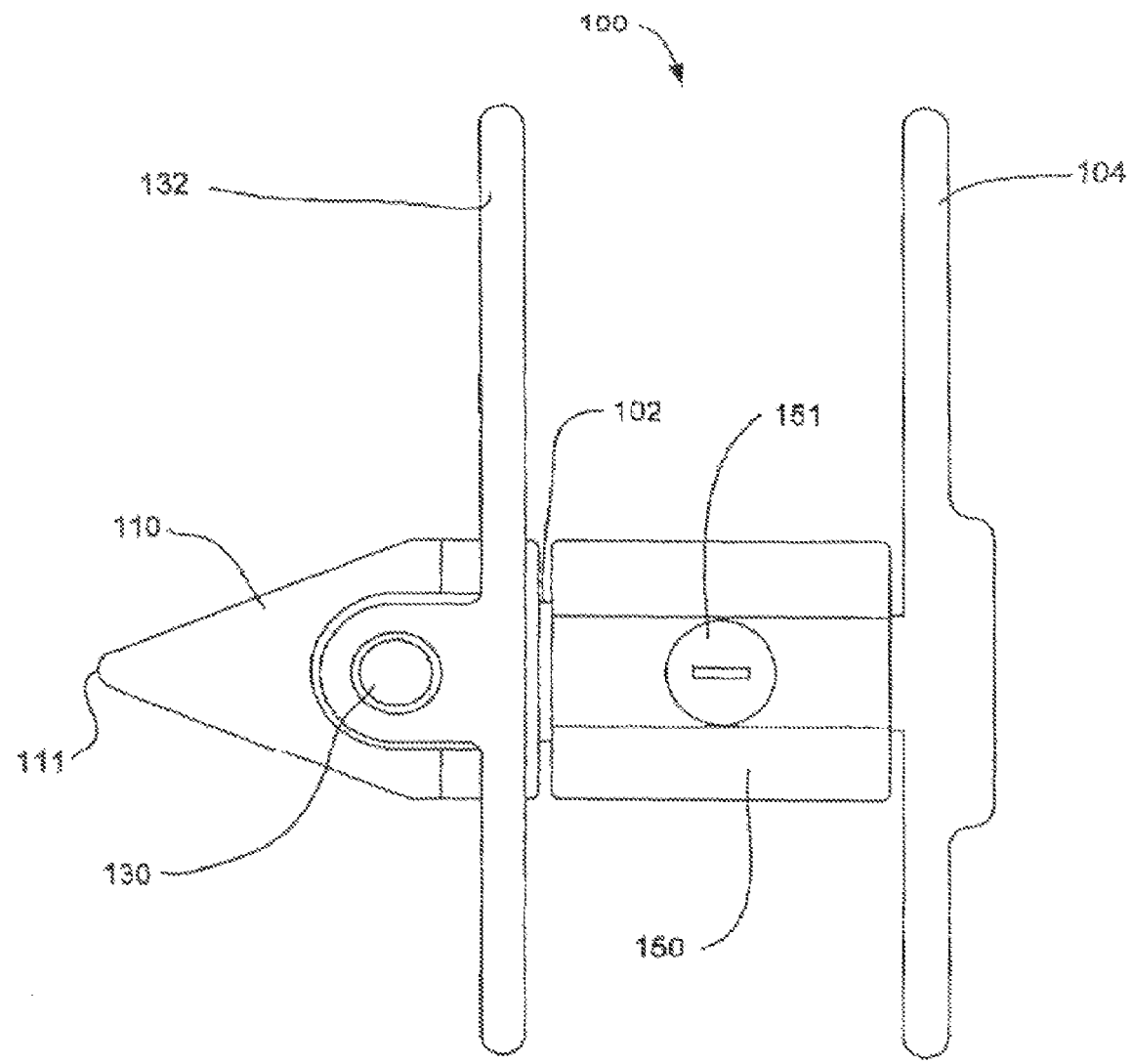
FIGS. 1A-1F.
Figure 1B:
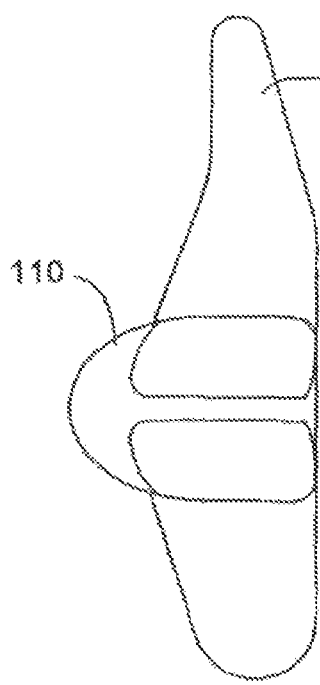
Figure 1C:
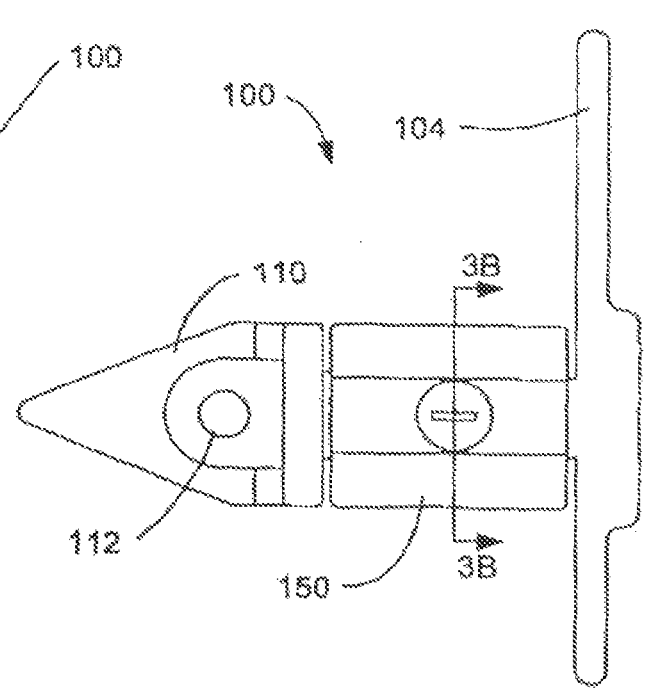
Figure 1D:
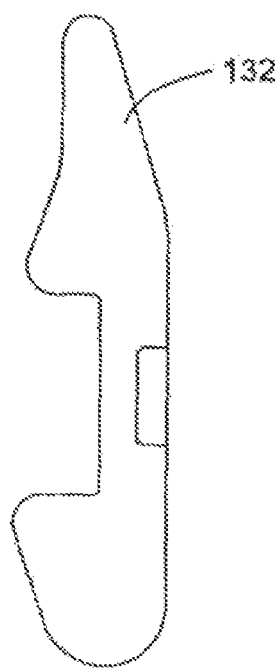
Figure 1E:
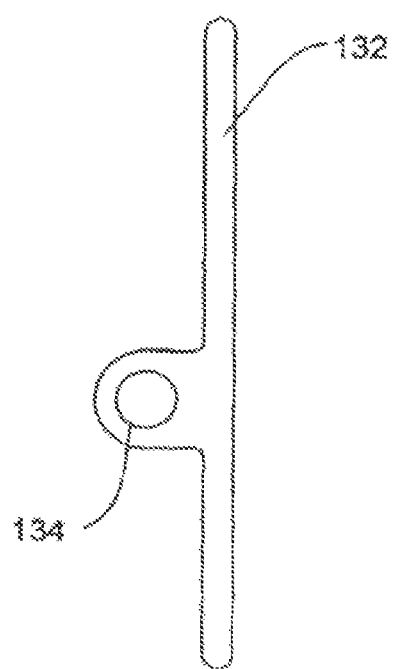
Figure 1F:
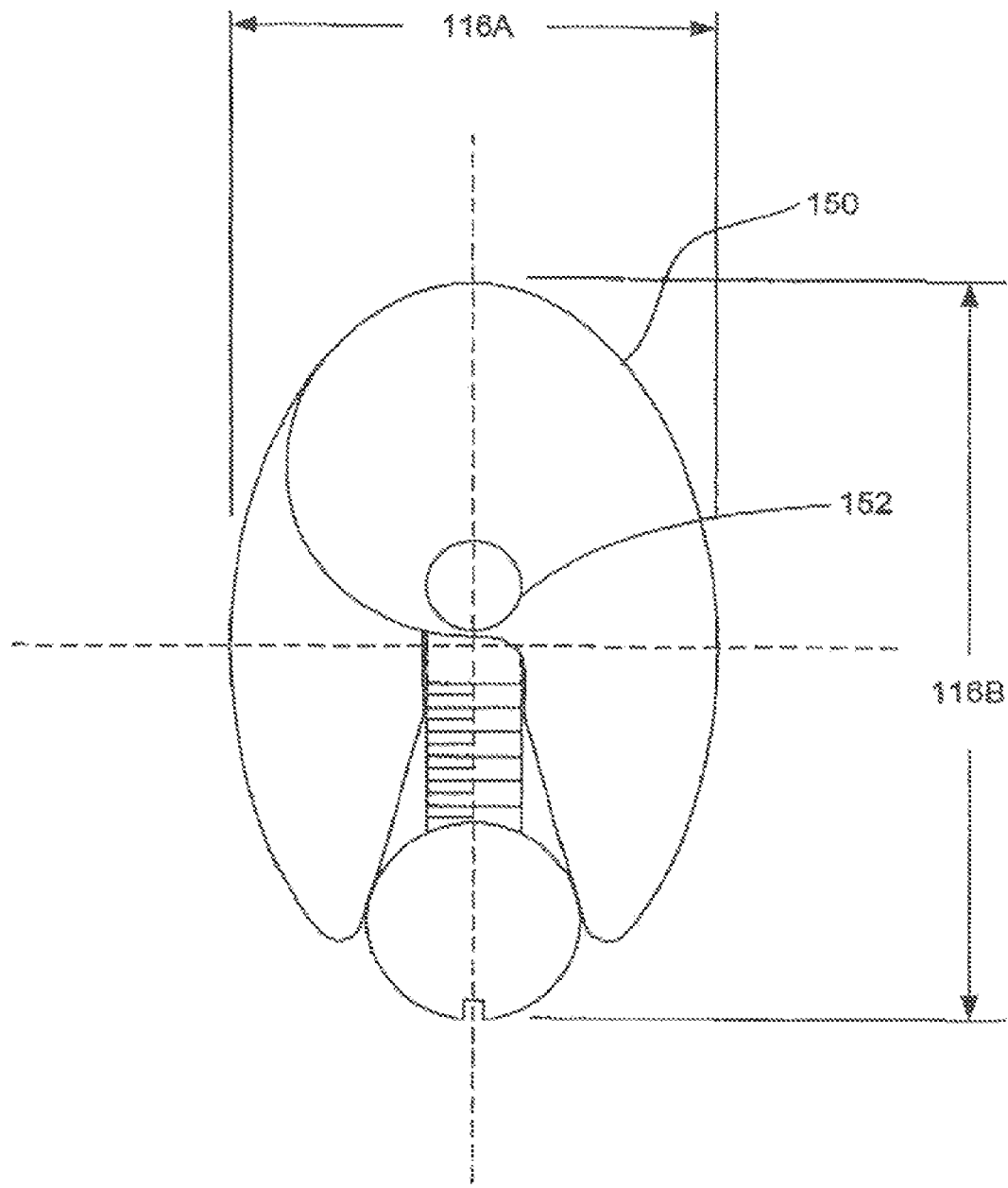

FIGS. 1A-1F illustrate an embodiment of an apparatus, or implant 100, suitable for use with the method of this invention. The implant 100 includes a first wing 104, a selectably expandable spacer 150 and a lead-in tissue expander or distraction guide 110. The implant further includes, as required, a second wing 132. As shown in FIG. 1A, first wing 104 and second wing 132 may have respective upper and lower winglets with respect to expandable spacer. As can be seen in FIG. 1A, a shaft 102 extends from the first wing 104 and is the body that connects the first wing to the distraction guide 110. Also, as can be seen in FIGS. 1A and 1B, the guide 110 in this particular embodiment is pointed in order to allow the implant to be inserted between, and, if necessary, to distract adjacent spinous processes. In this particular embodiment, the guide 110 has a wedge-shaped cross-section, expanding from the distal end 111 to the area where the second wing 132 can be optionally secured to the guide. FIGS. 1B and 1C illustrate an embodiment of the implant 100 with only a first wing 104.

As required, implant 100 can include a second wing 132 which fits over the guide 110 and is secured by a bolt 130 placed through aperture 134 of the second wing 132 to the threaded bore 112 located in the guide 110. As implanted, the first wing 104 is located adjacent to first sides of the spinous processes and the second wing 132 is located adjacent to second sides of the same spinous processes.

The spacer 150 is rotatably mounted about a shaft 102. The spacer 150 is positioned between the first wing 104 and the guide 110. The tissue expander 110 guides the spacer 150 into position between the spinous process of adjacent vertebrae. The spacer 150 includes a slotted sphere 151 that when rotated is positioned along a lead-screw, expanding or collapsing the spacer.

FIGS. 1F, 2A-B, 3A-B, and 5A-B illustrate a preferred embodiment of the spacer 150 wherein the shape of the spacer 150 is oval or elliptical in cross-section, although it can alternatively be circular or ovoid or race-track shaped in cross-section. It is to be understood that the spacer 150 can have other shapes as described throughout the specification and be within the spirit and scope of the invention. In a preferred embodiment, the spacer 150 includes a bore 152 extending the length of the spacer 150. The bore 152 of the spacer 150 is received over the shaft 102 of the implant 100 so that, as described above, the spacer can be rotated about the shaft 102. In these embodiments, the spacer 150 can have minor and major dimensions as follows:

| Minor Dimension (116a) | Major Dimension (116b) |
|---|---|
| 6 mm | 10 mm |
| 8 mm | 10.75 mm |
| 12 mm | 14 mm |
| 6 mm | 12.5 mm |
| 8 mm | 12.5 mm |
| 10 mm | 12.5 mm |

One advantage of the use of the spacer 150, as depicted in the embodiment of FIG. 1A, is that the spacer 150 can be partially rotated and repositioned with respect to the first wing 104 in order to optimize positioning of the implant 100 between spinous processes. It is to be understood that the cortical bone or the outer bone of the spinous processes is stronger at an anterior position adjacent to the vertebral bodies of the vertebra than at a posterior position distally located from the vertebral bodies. Also, biomechanically for load bearing, it is advantageous for the spacer 150 to be close to the vertebral bodies. In order to facilitate this and to accommodate the anatomical form of the bone structures, as the implant is inserted between the spinous processes and/or urged toward the vertebral bodies, the spacer 150 rotates relative to the wings, such as wing 104, so that the spacer 150 is optimally positioned between the spinous processes, and the wing 104 is optimally positioned relative to the spinous processes.

In another embodiment, the spacer 150 has a cross-section with a major dimension and a minor dimension, wherein the major dimension is greater than the minor dimension, and, for example, less than about two times the minor dimension. It is to be understood that the spacer 150 can be fabricated from somewhat flexible and/or deflectable material.

In this embodiment the spacer is made out of a polymer, more specifically, the polymer is a thermoplastic. Still more specifically, the polymer is a polyketone known as polyetheretherketone (PEEK™). Still more specifically, the material is PEEK 450G, which is an unfilled PEEK approved for medical implantation available from Victrex of Lancashire, Great Britain. (Victrex is located at www.matweb.com or see Boedeker www.boedeker.com). Other sources of this material include Gharda, located in Panoli, India (www.ghardapolymers.com).

The spacer 150 can be formed by extrusion, injection, compression molding and/or machining techniques. This material has appropriate physical and mechanical properties and is suitable for carrying and spreading the physical load between the spinous process. For example, in this embodiment, the PEEK has the following approximate properties:

| | |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

It should be noted that the material selected may also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

In this embodiment, as described above, the spacer 150 is manufactured from polyetheretherketone (PEEK™), available from Victrex. As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. The spacer can also be comprised of polyetherketoneketone (PEKK).

Other materials that can be used include polyetherketone (PEK), polyetherketoneetherketoneketone (PEKEKK), and polyetheretherketoneketone (PEEKK), and generally a polyaryletheretherketone. Further other polyketones can be used as well as other thermoplastics. The spacer can also be made of titanium.

Reference to appropriate polymers that can be used in the spacer can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials."

Other materials such as Bionate.R™, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Figure 2A:
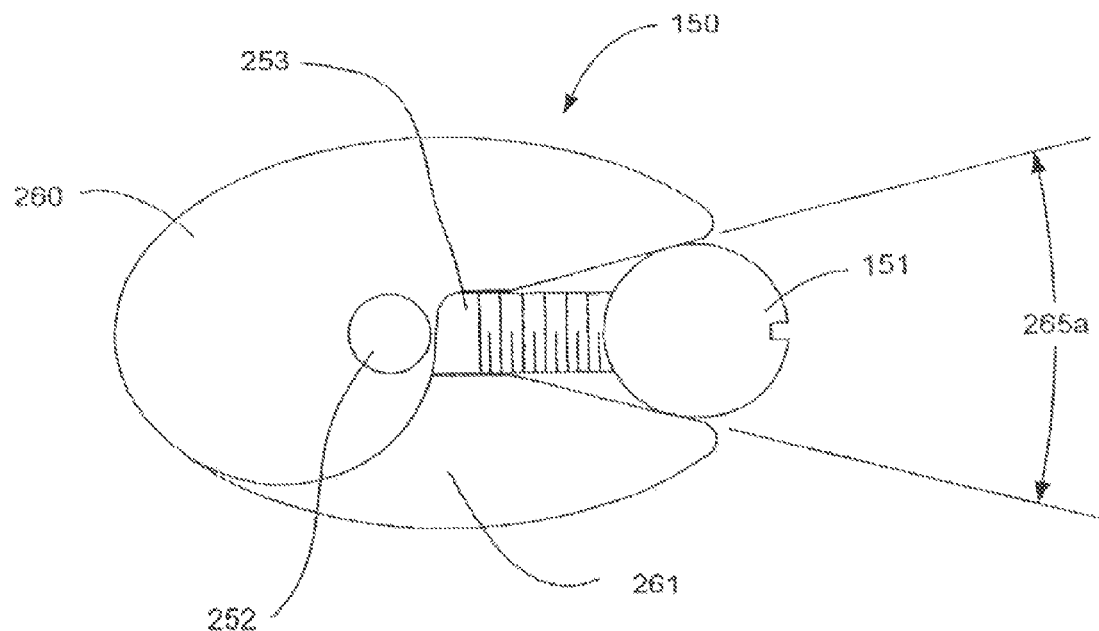
FIGS. 2A and 2B.

A preferred embodiment of the spacer is illustrated in FIGS. 2A-5. In FIGS. 2A and 2B the spacer 150 includes a first portion 260 pivotably or rotatably coupled with a second portion 261 by a hinge (shown in FIG. 4). Both the first portion 260 and the second portion 261 have tapered distal ends that form an acute angle between the two portions. FIG. 2A illustrates the acute angle 265a formed when the spacer 150 is in the unexpanded position. The first portion 260 has a bore 252 through which the shaft 102, shown in FIG. 1A, is received, connecting the first wing 104 with the guide 110 and connecting the spacer 150 with the implant 100. The bore 252 allows the spacer 150 to partially rotate about the shaft 102. The second portion 261 of the spacer 150 also has a bore that is located behind and aligned with the bore 252, shown in FIG. 2A. This bore is also received on the shaft 102 so that both the first and second portions of the spacer 150 can rotate about the shaft 102. A threaded screw 253 protrudes through the angle 265 a formed by the tapered distal ends of the portions. The end of the threaded screw 253 also has a bore that aligns with the bores of the first and second portions of the spacer 150 and is received on the shaft 102 and can rotate about the shaft 102. A slotted sphere 151 is connected with the distal end of screw 253. In the least expanded position, the slotted sphere 151 is at the farthest point of travel away from the proximal end of the screw 253 FIG. 2A.

Figure 2B:
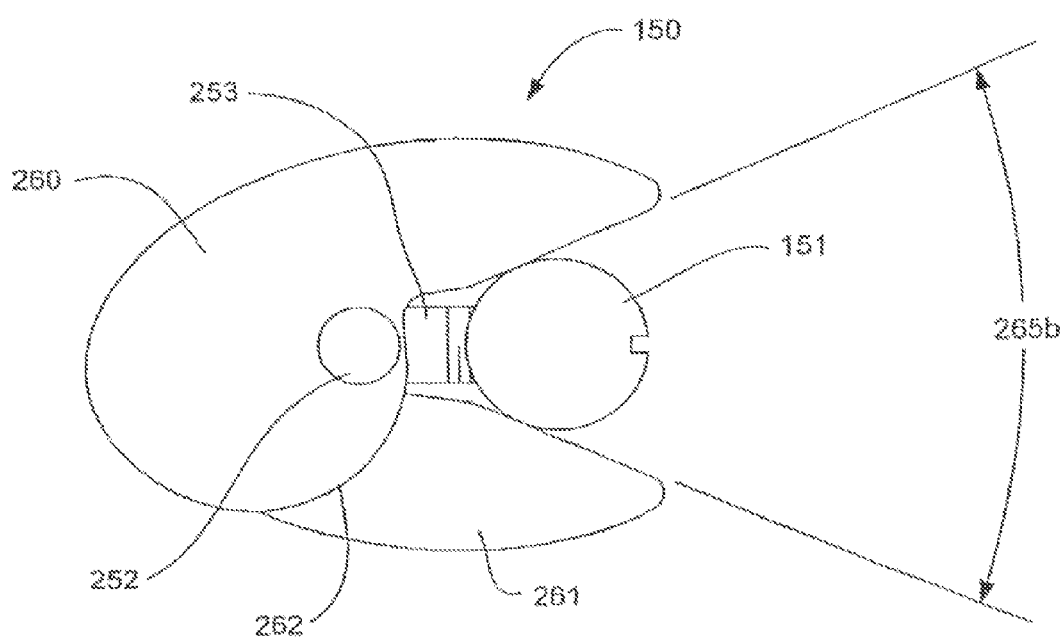

FIG. 2B illustrates the acute angle 265b formed when the spacer 150 is in the fully expanded position. The slotted sphere 151 is rotated such that the sphere travels toward the proximal end of the threaded screw 253. As the slotted sphere 151 travels toward the proximal end of the screw 253, the sphere 151 forces the tapered distal ends of the portions 260, 261 apart. As the distal ends of the portions are forced apart, the first portion 260 and the second portion 261 rotate in opposite directions about a common hinge 463 (shown in FIG. 4), sliding along the contact surface 262. As the acute angle formed by the distal ends of the portions increases, the height of the spacer 150 expands.

Figure 3A:
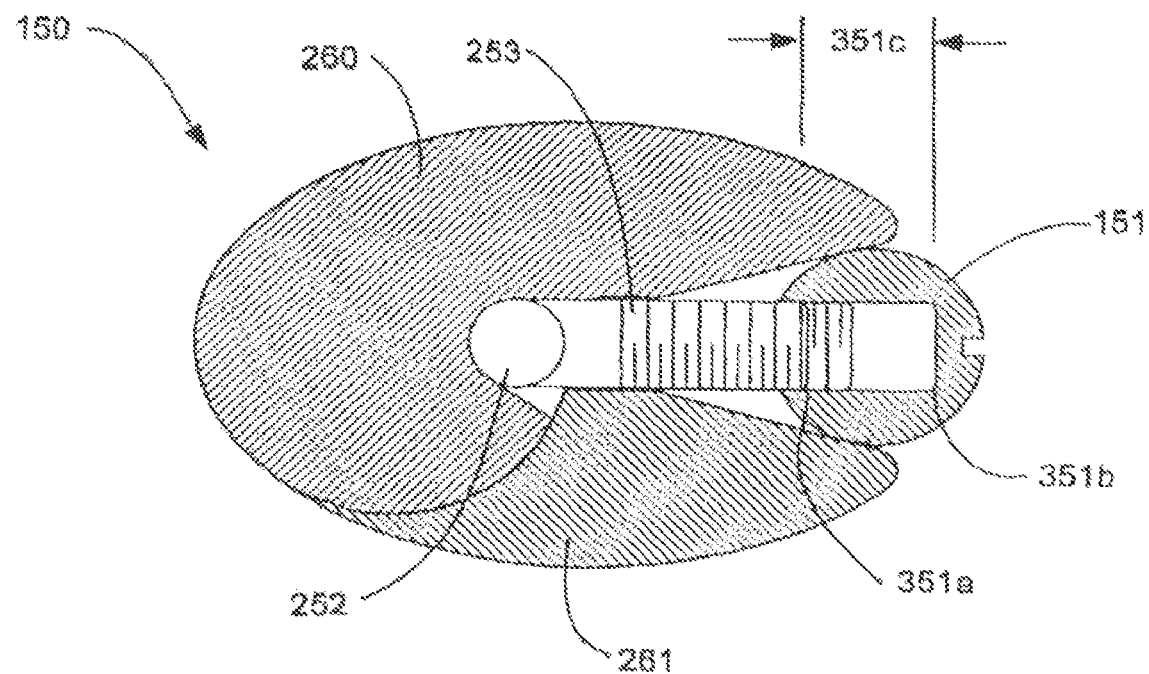
FIGS. 3A and 3B.
Figure 3B:
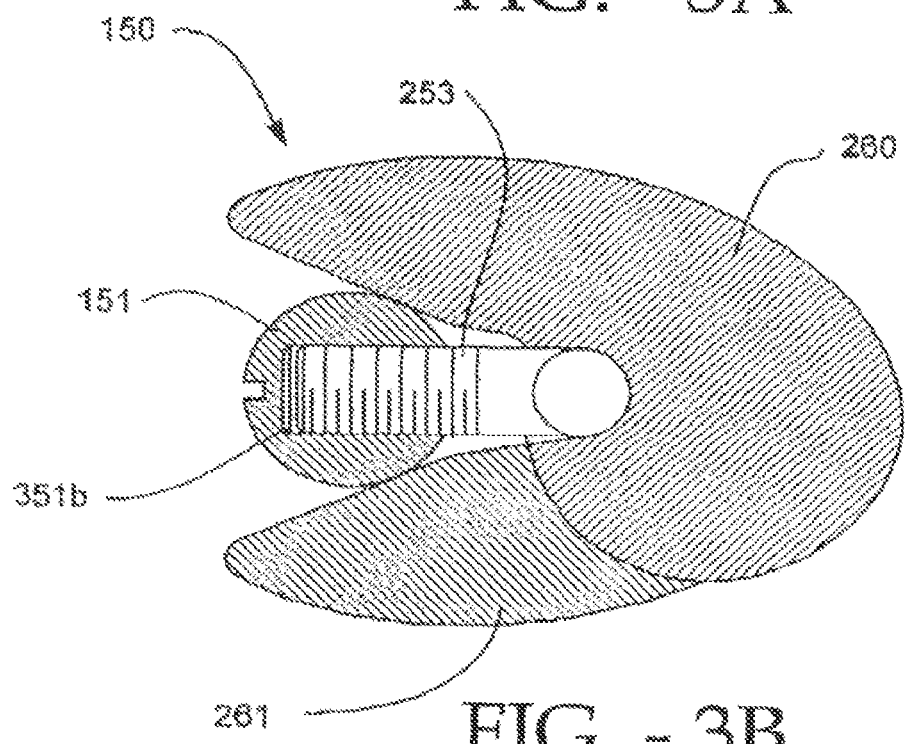

FIGS. 3A and 3B illustrate in cross-section the preferred embodiment of the selectably expandable spacer described in reference to FIGS. 2A and 2B. The slotted sphere 151 has a threaded cavity for receiving the threaded screw 253 when the sphere 151 is rotated. The slotted sphere 151 travels the distance 351c such that the distal end of the screw 253 moves from position 351a to position 351b along the threaded cavity of the sphere when adjusted from an unexpanded to a fully expanded position. When rotated in the opposite direction, the slotted sphere 151 moves away from the proximal end of the screw 253, collapsing the spacer 150. FIG. 3B illustrates the spacer 150 in a fully expanded position with the distal end of the screw 253 at the maximum position 351b in the threaded cavity of the slotted sphere 151. It is to be understood that portions the 260, 261 of the spacer 150 can be biased to the closed position shown in FIG. 3A. The biasing can be accomplished by a spring that is coiled in or about the bore of the spacer that receives the shaft 102. Such a spring would be connected to both of the portions 260, 261 of the spacer 150.

The first and second portions of the spacer 150 in combination, can have a cross-section that is elliptical, oval, ovoid, football-shaped, circular-shaped, rectangular with rounded ends (where the cross-section has two somewhat flattened surfaces and two rounded surfaces similar to the effect of a flattened ellipse) or race-track shaped. Further, the first and second portions can have different cross-sectional shapes relative to each other. At least the minor dimension (the height) of the spacer is between 6 mm and 14 mm. Typically, the minor outer dimension is one of 6 mm, 8 mm, 10 mm, 12 mm, and 14 mm. The different sizes and selectable expandability enable the spacer to accommodate different sized patients.

As discussed above, the spacer 150 and its components, including either the first or second portions, or both, can be made of a number of materials. Suitable materials can include polymers, such as, for example, polyetheretherketone (PEEK™), as well as other materials described above, including titanium. Such materials can be deflectable and flexible depending on the configuration of the spacer 150.

Further, the deflectable or flexible material can have a graduated stiffness to help gradually distribute the load when the spinous processes place a force upon the exterior surface of the spacer. This can be accomplished by forming multiple layers of the deflectable or flexible material with decreasing stiffness or hardness from the center of the spacer outwardly. Alternatively, the material can have a higher stiffness or hardness in the center of the inner spacer.

Figure 4:
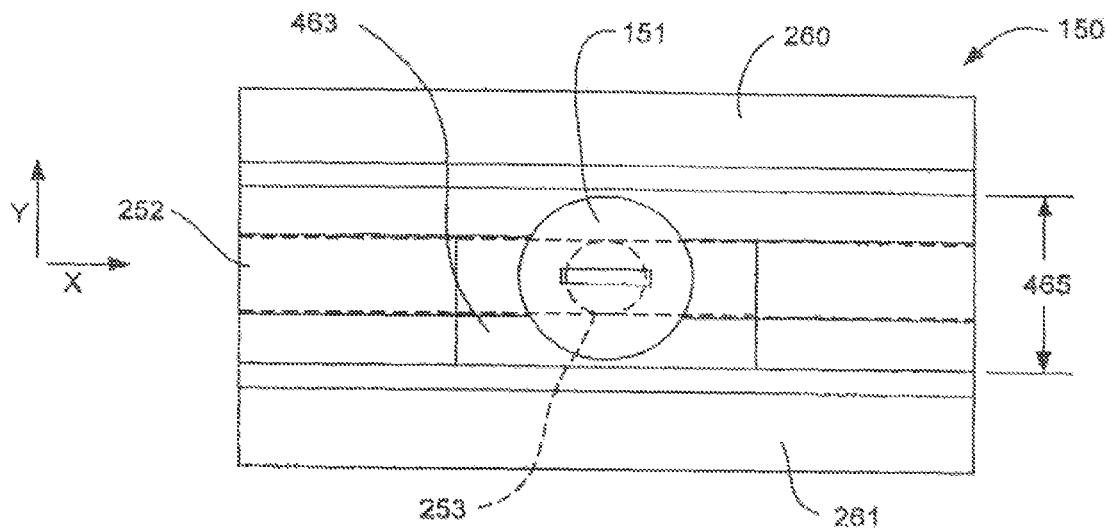
FIG. 4 is a front side view of an embodiment of the selectably adjustable spacer.

Referring to FIG. 4, the slotted sphere 151 is positioned approximately equidistant from a first and second ends of the spacer 150, distributing the parting force of the sphere 151 so as not to create disproportionate stress on either side of the spacer 150.

A hinge 463 couples a first portion 260 with a second portion 261, such that the two portions pivot about the hinge 463, expanding or collapsing the gap 465.

Figure 5A:
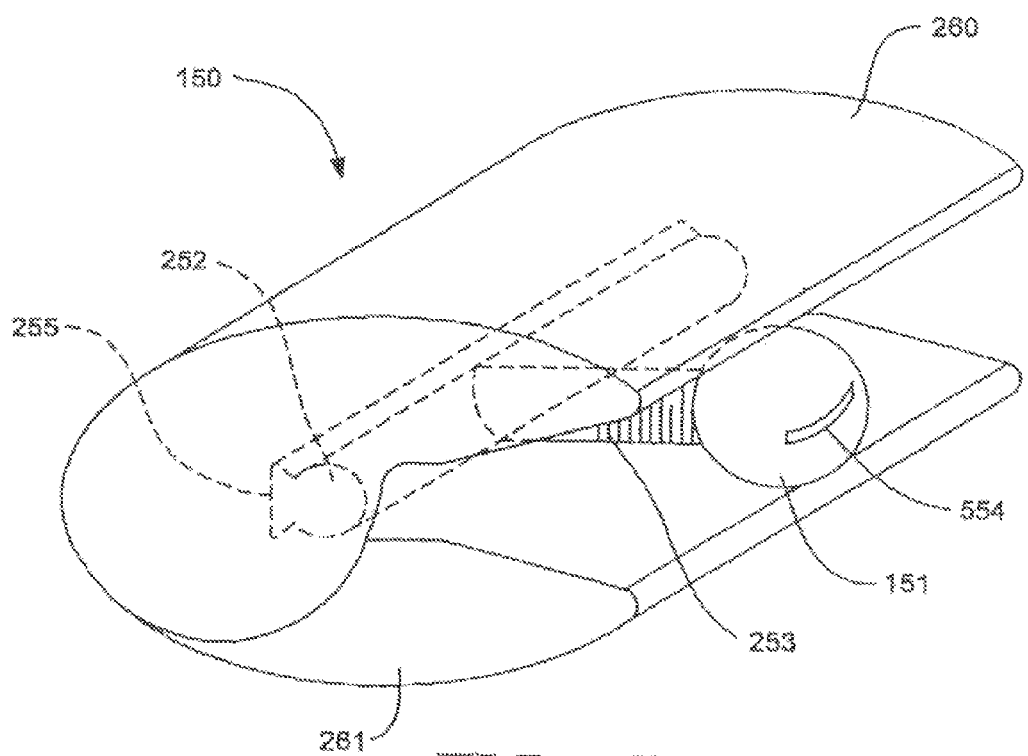
FIG. 5A is a perspective view of an embodiment of the selectably adjustable spacer.

A perspective view is provided in FIG. 5A, showing the clam-shape of the preferred embodiment of the spacer 150. The implant 100 is positioned between the adjacent vertebrae so as to permit access to the slot 554 from a posterior direction both during and after surgery. Post-surgery adjustment, for example, may be is made using tool 164 that accesses slot 554 through cannula 162 inserted through the patient's back. Convenient access to the slot 554 is important for reducing patient discomfort and procedure complication.

The bore 252 provides a sleeve for the shaft 102, and also limits the rotation of the spacer 150 about the shaft 102. Limiting the rotation of the spacer 150 can be accomplished, for example, by providing a slot 255 in the bore 252 and a key on the shaft 102, or vice-versa. One of skill in the art can appreciate that different mechanisms and geometries can be used to limit spacer rotation. Reference is also made to a copending U.S. patent application entitled "Spinal Implants, Insertion Instruments, and Methods of Use," filed on Mar. 5, 2001, as U.S. patent application Ser. No. 09/799,470 (KLYC-1027 USI), which is incorporated herein by reference and which discloses an implant which has a spacer with a slot and an implantation tool that includes a probe that engages the slot in order to position the spacer relative to the implantation tool for desirable initial positioning of the space relative to the spinous processes. Such a mechanism can be used by itself or in addition to the above discussed keyway and key for purposes of positioning the sphere 151 so that the height of the spacer 150 can be selectively adjusted during the initial surgical procedure or, thereafter, should such adjustment be desirable due, for example, to the need for more distraction between the spinous processes.

Figure 5B:
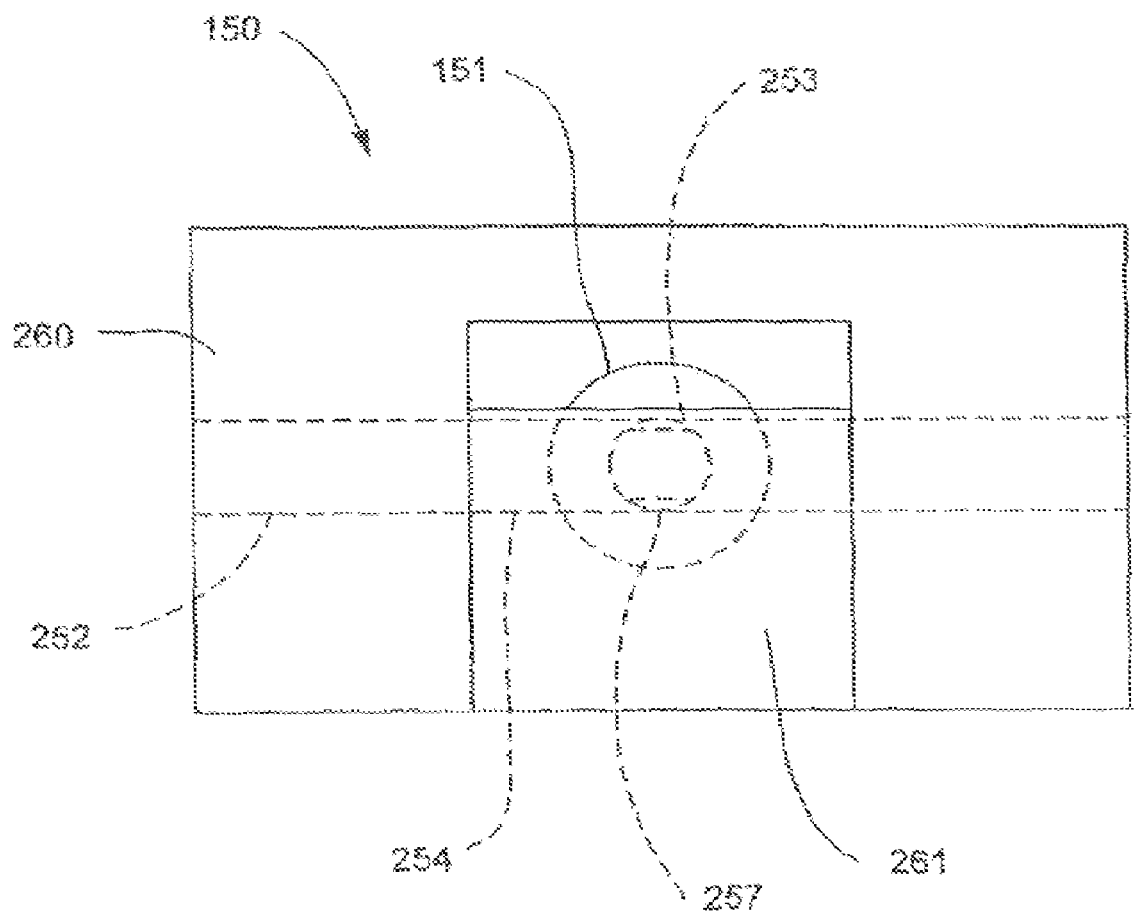
FIG. 5B is a back view of another embodiment of the spacer similar to that shown in FIG. 5A with a mechanism for allowing the spacer to expand.

FIG. 5B depicts the back of another embodiment of the spacer 150 of the implant 100 of the invention. FIG. 5B is similar to a back view of the embodiment depicted in FIG. 4. In FIG. 5B, the spacer 150 includes the first and second portions 260, 261, respectively. The first portion includes a bore 252 that receives the shaft 102 and the second portion includes bore 254 that also receives the shaft 102. In addition, the screw 253 is shown with a portion of the sphere 151 that is used to adjust the height of the spacer 150. The screw 253 includes a bore 257 that also receives the shaft 102. Thus, the first and second portions of the spacer and the screw are rotatable about the shaft.

Figure 6A:
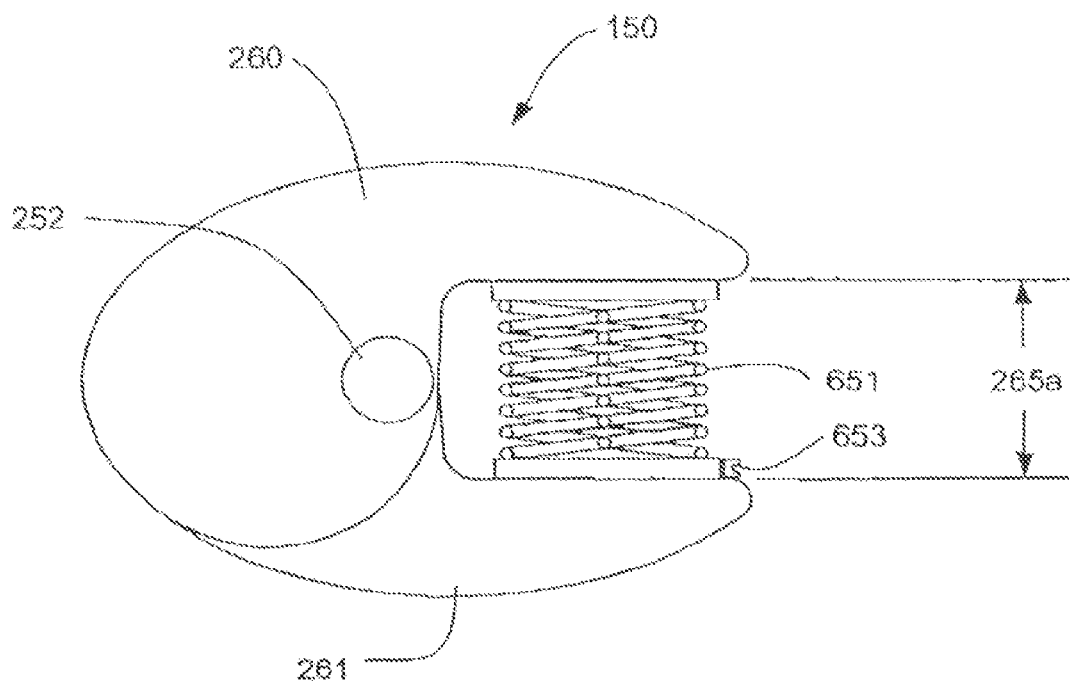
FIGS. 6A and 6B.
Figure 6B:
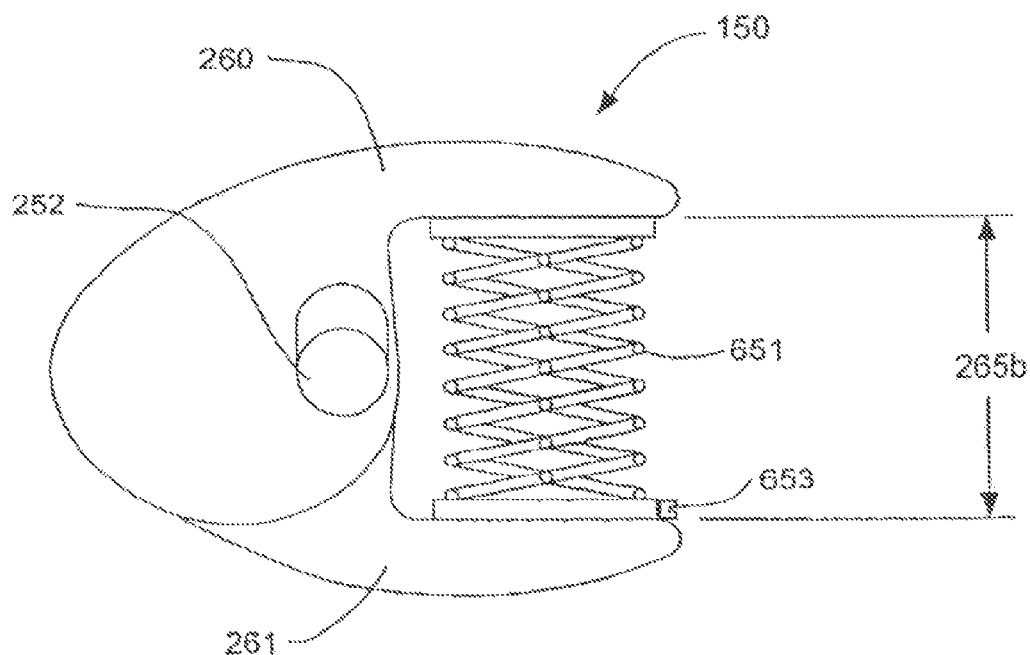

One of skill in the art can also appreciate the different expansion mechanisms that can be employed to expand the spacer 150. For example, an expansion mechanism could include: pistons, ratchets, cams, jacks, or other machines. FIGS. 6A and 6B illustrate one alternative embodiment in which a jack 651 is used to expand the spacer 150. The jack 651 is expanded or collapsed by rotating a slotted screw 653, thereby increasing or decreasing the gap 665. FIG. 6A shows the spacer 150 in an unexpanded position with a narrow gap 665a.

FIG. 6B illustrates another alternative embodiment utilizing a jack, whereby the hinge 462 can allow for translation of the first and second portions in the y-direction as well as for rotation about the hinge 462, thereby reducing the stresses on the side of the jack closest to the hinge caused by uneven compression when the gap 665b expands. For the embodiment in FIGS. 6A and 6B any of the above devices for allowing the first portion of the spacer to move relative to the second portion of the spacer can be employed, as well as other known methods, and be within the spirit and scope of the invention.

Figure 7:
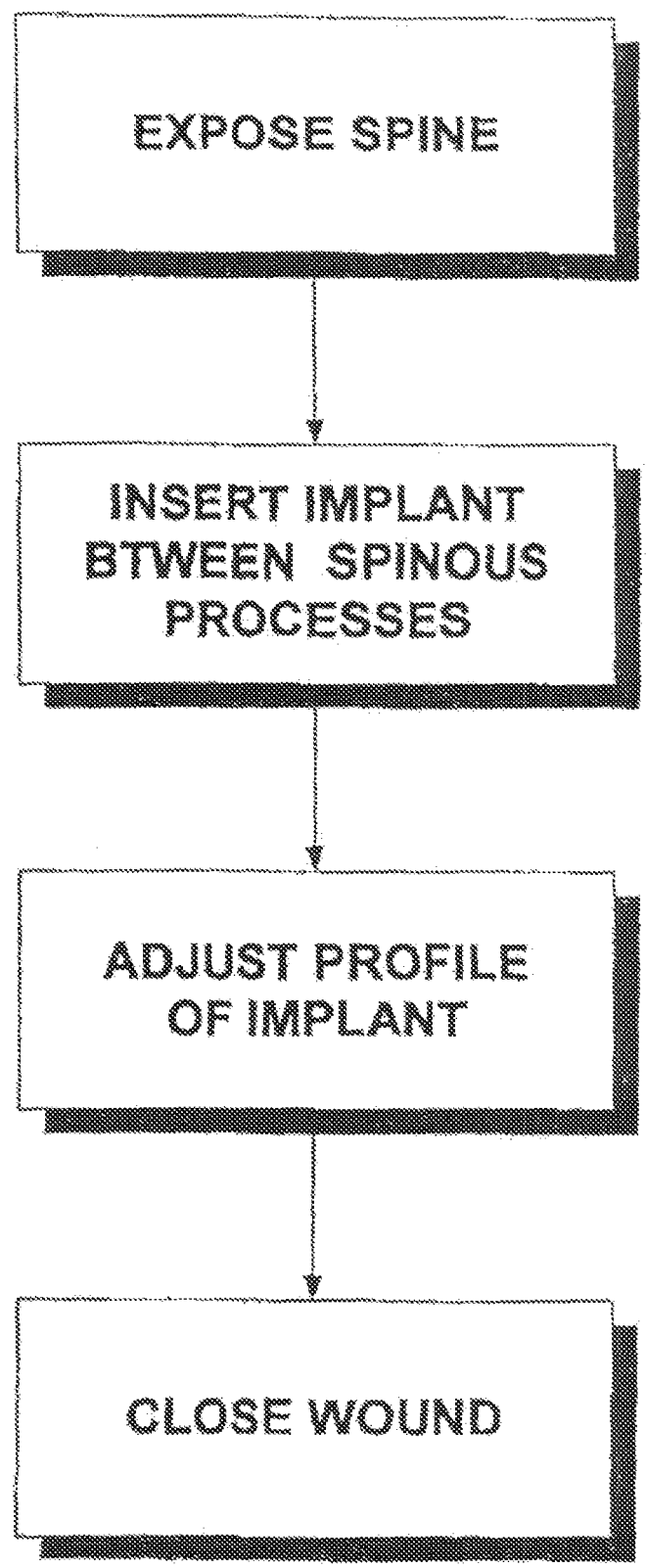
Figure 8:
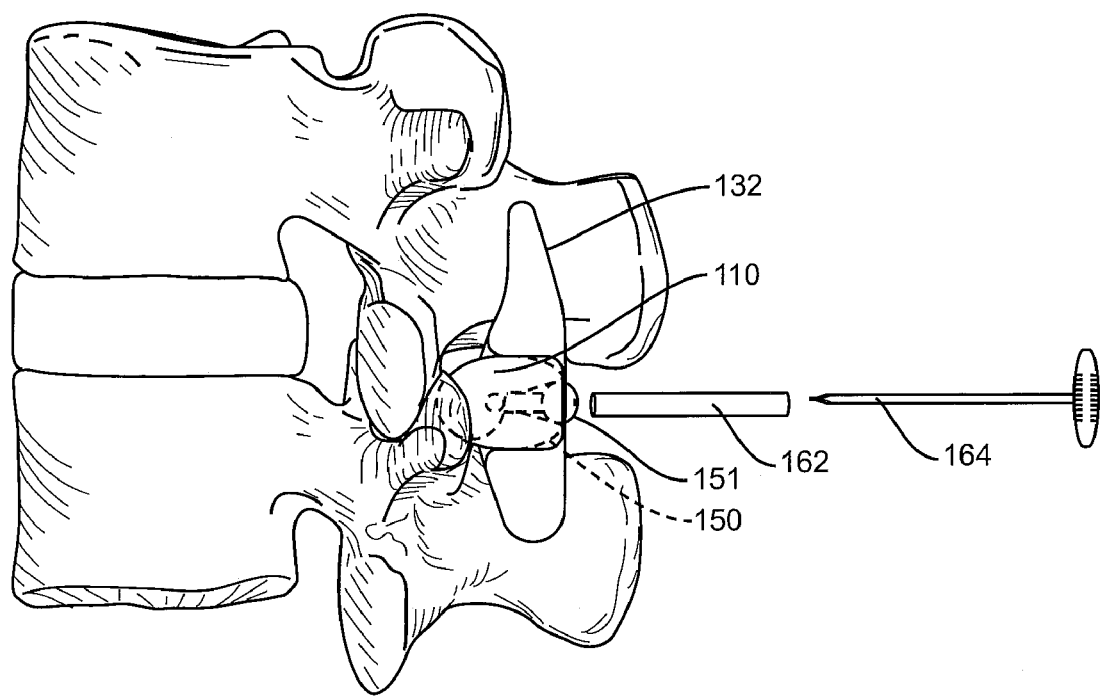
FIG. 8 shows a post-surgery adjustment using a tool and a cannula.

The preferred method for inserting the implant between adjacent vertebrae is block-diagramed in FIG. 7. The method requires that the spine be surgically exposed. The implant is then inserted between the spinous processes, with the wedge shape of the guide forcing tissue apart to create room for the implant. Once the implant is in place, with the spacer between adjacent vertebrae, the profile of the implant is adjusted by expanding or collapsing the spacer using a tool for operating the expansion mechanism. The wound is then closed.

The implant can subsequently be readjusted with the insertion of a cannula through which a tool is inserted for operating the expansion mechanism.

The embodiment of this apparatus as well as the several other apparatuses described herein, act to limit extension (backward bending) of the spine. These apparatuses, however, do not inhibit the flexion (forward bending) of the spinal column.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and their equivalence.

What is claimed is:

1. An implant adapted to be placed between upper and lower spinous processes comprising:
   a spacer adapted to fit between spinous processes;
   first and second winglets extending from a lateral first side of the spacer and third and fourth winglets extending from a second lateral side opposite the first lateral side of the spacer; the first and third winglets extending upwardly from the spacer and the second and fourth winglets extending downwardly from the spacer; the spacer distinct from the winglets and having upper and lower portions;
   the spacer upper portion disposed between the first and third winglets and the spacer lower portion disposed between the second and fourth winglets;
   the spacer upper portion pivotally mounted relative to the third winglet along a pivot axis that extends from the first lateral side of the spacer to the second lateral side of the spacer and is disposed generally transverse to the first and second winglets; the spacer upper portion moveable relative to the spacer lower portion; and
   wherein the implant is configured such that, when the implant is disposed between the spinous processes, the first and third winglets extend along a first and second lateral side respectively of the upper spinous process, and the second and fourth winglets extend along a first and second lateral side respectively of the lower spinous process.

2. The implant of claim 1 wherein the spacer has an elliptical shape in at least one dimension wherein a height of the spacer in that dimension is less than a length of the spacer in another dimension.

3. The implant of claim 1 wherein the upper portion and lower portion of the spacer are connected by a hinge.

4. The implant of claim 1 wherein the upper portion and the lower portion each have a curved surface and a height adjuster contacting surface opposite the curved surface.

5. The implant of claim 1 further comprising a jack to adjust the height of the spacer.

6. The implant of claim 5 where the jack is adjustable between a greater profile and a lesser profile by turning a screw.

7. The implant of claim 1 further comprising a fastener disposed between the third and fourth winglets, wherein the third and fourth winglets are collinear and formed by a common element.

8. An implant adapted to be placed between spinous processes comprising:
   a spacer having upper and lower members movable relative to each other such that the spacer has an adjustable height;
   at least one of the upper or lower members having a bore;
   a shaft received in the bore, the shaft extending from a first wing;
   a distraction guide disposed generally opposite from the first wing and extending generally transverse to the first wing;
   an engaging screw extending generally transverse to the bore and the shaft and operative to lock the height of the spacer; and
   the first wing forming upper and lower saddles with the spacer upper and lower members respectively;
   wherein a minimum distance between the upper and lower saddles is adjustable while a relative angular orientation between the upper and lower saddles remains constant;
   wherein when the implant is disposed between the spinous processes, the engaging screw and the first wing extend generally parallel to a sagittal plane defined by the spinous processes.

9. The implant of claim 8 wherein the spacer has an elliptical shape.

10. The implant of claim 8 wherein the upper member and the lower member of the spacer are connected proximal to an end thereof by a hinge.

11. The implant of claim 8 wherein the upper member and the lower member each have a curved surface and a height adjuster surface opposite the curved surface.

12. The implant of claim 8 further comprising a jack to adjust the height of the spacer.

13. The implant of claim 12 wherein the jack engages the upper member and lower member of the spacer to maintain the height.

14. The implant of claim 12 wherein the jack is adjustable between a greater profile and a lesser profile by turning a screw.

15. A method of adjusting an implanted interspinous implant having a body having a shaft extending therefrom, a spacer pivotally mounted on the body for pivoting on an axis that extends through a sagittal plane defined by adjacent spinous processes disposed on either side of the implant, and a screw for adjusting the space between a first portion and a second portion of the spacer, the method comprising:

accessing the screw of the implanted interspinous implant through an incision with a cannula; and adjusting a profile of the implant with a tool accessed through the cannula by turning the screw of the implant in one of a first direction and a second direction.

\* \* \* \* \*